(12) United States Patent
Mi et al.

(10) Patent No.: US 7,912,548 B2
(45) Date of Patent: Mar. 22, 2011

(54) RESONANT STRUCTURES FOR IMPLANTABLE DEVICES

(75) Inventors: Bin Mi, Plymouth, MN (US); Abhijeet V. Chavan, Maple Grove, MN (US); John H. Tangren, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 847 days.

(21) Appl. No.: 11/781,023

(22) Filed: Jul. 20, 2007

(65) Prior Publication Data

US 2008/0021510 A1 Jan. 24, 2008

Related U.S. Application Data

(60) Provisional application No. 60/820,057, filed on Jul. 21, 2006.

(51) Int. Cl.
*A61N 1/375* (2006.01)
(52) U.S. Cl. .......................................................... 607/36
(58) Field of Classification Search .............. 607/36–37, 607/2
See application file for complete search history.

(56) References Cited

U.S. PATENT DOCUMENTS

| | | |
|---|---|---|
| 2,967,957 A | 1/1961 | Massa |
| 3,568,661 A | 3/1971 | Franklin |
| 3,676,720 A | 7/1972 | Libby et al. |
| 3,757,770 A | 9/1973 | Brayshaw et al. |
| 3,792,204 A | 2/1974 | Murayama et al. |
| 3,798,473 A | 3/1974 | Murayama et al. |
| 3,832,580 A | 8/1974 | Yamamuro et al. |
| 3,894,198 A | 7/1975 | Murayama et al. |
| 3,940,637 A | 2/1976 | Ohigashi et al. |
| 3,978,353 A | 8/1976 | Kinoshita |
| 4,008,408 A | 2/1977 | Kodama |
| 4,051,455 A | 9/1977 | Fowler |
| 4,056,742 A | 11/1977 | Tibbetts |

(Continued)

FOREIGN PATENT DOCUMENTS

DE 3222349 1/1984

(Continued)

OTHER PUBLICATIONS

International Search Report and Written Opinion of International No. PCT/US2006/033273, filed Aug. 25, 2006, both mailed Jan. 19, 2007.

(Continued)

*Primary Examiner* — Scott M Getzow
*Assistant Examiner* — Amanda Patton
(74) *Attorney, Agent, or Firm* — Faegre & Benson LLP (57) ABSTRACT

An implantable medical device comprising a housing and a limiting structure defining a resonant region in the housing. An acoustic transducer is connected to the limiting structure and extends into the resonant region so that the resonant region mechanically amplifies the deformation of the acoustic transducer at a resonant frequency. An implantable medical device comprising a housing and a limiting structure defining a resonant region in the housing. An acoustic transducer having the shape of a beam is mechanically coupled to the limiting structure and partially extends into the resonant region so that the resonant region mechanically amplifies the deformation of the acoustic transducer at a resonant frequency. An implantable medical device comprising a housing, an acoustic transducer coupled to the housing, and a means for mechanically amplifying the deformation of the acoustic transducer at a resonant frequency. The means defines a resonant region in the housing.

18 Claims, 10 Drawing Sheets

U.S. PATENT DOCUMENTS

| | | | |
|---|---|---|---|
| 4,064,375 A | 12/1977 | Russell et al. | |
| 4,096,756 A | 6/1978 | Alphonse | |
| 4,127,110 A | 11/1978 | Bullara | |
| 4,170,742 A | 10/1979 | Itagaki et al. | |
| 4,181,864 A | 1/1980 | Etzold | |
| 4,227,407 A | 10/1980 | Drost | |
| 4,281,484 A | 8/1981 | Massa | |
| 4,431,873 A | 2/1984 | Dunn et al. | |
| 4,433,400 A | 2/1984 | De Reggi et al. | |
| 4,440,983 A | 4/1984 | Facoetti et al. | |
| 4,456,850 A | 6/1984 | Inoue et al. | |
| 4,481,950 A | 11/1984 | Duggan | |
| 4,517,665 A | 5/1985 | De Reggi et al. | |
| 4,519,401 A | 5/1985 | Ko et al. | |
| 4,541,431 A | 9/1985 | Ibrahim et al. | |
| 4,558,249 A | 12/1985 | Lerch et al. | |
| 4,577,132 A | 3/1986 | Ohigashi et al. | |
| 4,580,074 A | 4/1986 | Gilman | |
| 4,593,703 A | 6/1986 | Cosman | |
| 4,600,855 A | 7/1986 | Strachan | |
| 4,642,508 A | 2/1987 | Suzuki et al. | |
| 4,653,036 A | 3/1987 | Harris et al. | |
| 4,653,508 A | 3/1987 | Cosman | |
| 4,660,568 A | 4/1987 | Cosman | |
| 4,672,976 A | 6/1987 | Kroll | |
| 4,676,255 A | 6/1987 | Cosman | |
| 4,677,337 A | 6/1987 | Kleinschmidt et al. | |
| 4,781,715 A | 11/1988 | Wurzel | |
| 4,793,825 A | 12/1988 | Benjamin et al. | |
| 4,835,435 A | 5/1989 | Yeung et al. | |
| 4,846,191 A | 7/1989 | Brockway et al. | |
| 4,911,172 A | 3/1990 | Bui et al. | |
| 4,958,100 A | 9/1990 | Crawley et al. | |
| 4,992,692 A | 2/1991 | Dias | |
| 5,012,815 A | 5/1991 | Bennett, Jr. et al. | |
| 5,024,224 A | 6/1991 | Engebretson | |
| 5,088,576 A | 2/1992 | Potthoff et al. | |
| 5,113,859 A | 5/1992 | Funke | |
| 5,160,870 A | 11/1992 | Carson et al. | |
| 5,178,153 A | 1/1993 | Einzig | |
| 5,283,397 A | 2/1994 | Pavlovic | |
| 5,289,821 A | 3/1994 | Swartz | |
| 5,300,875 A | 4/1994 | Tuttle | |
| 5,314,457 A | 5/1994 | Jeutter et al. | |
| 5,339,290 A | 8/1994 | Greenstein | |
| 5,367,500 A | 11/1994 | Ng | |
| 5,381,067 A | 1/1995 | Greenstein et al. | |
| 5,381,386 A | 1/1995 | Lum et al. | |
| 5,410,587 A | 4/1995 | Grunwell | |
| 5,411,551 A | 5/1995 | Winston et al. | |
| 5,423,334 A | 6/1995 | Jordan | |
| 5,438,553 A | 8/1995 | Wilson et al. | |
| 5,476,488 A | 12/1995 | Morgan et al. | |
| 5,483,501 A | 1/1996 | Park et al. | |
| 5,488,954 A | 2/1996 | Sleva et al. | |
| 5,495,137 A | 2/1996 | Park et al. | |
| 5,554,177 A | 9/1996 | Kieval et al. | |
| 5,562,714 A | 10/1996 | Grevious | |
| 5,571,152 A | 11/1996 | Chen et al. | |
| 5,628,782 A | 5/1997 | Myers et al. | |
| 5,679,026 A | 10/1997 | Fain et al. | |
| 5,704,352 A | 1/1998 | Tremblay et al. | |
| 5,733,313 A | 3/1998 | Barreras, Sr. et al. | |
| 5,735,887 A | 4/1998 | Barreras, Sr. et al. | |
| 5,741,316 A | 4/1998 | Chen et al. | |
| 5,749,909 A | 5/1998 | Schroeppel et al. | |
| 5,757,104 A | 5/1998 | Getman et al. | |
| 5,792,195 A | 8/1998 | Carlson et al. | |
| 5,807,258 A | 9/1998 | Cimochowski et al. | |
| 5,825,117 A | 10/1998 | Ossmann et al. | |
| 5,832,924 A | 11/1998 | Archibald et al. | |
| 5,833,603 A | 11/1998 | Kovacs et al. | |
| 5,843,135 A | 12/1998 | Weijand et al. | |
| 5,870,351 A | 2/1999 | Ladabaum et al. | |
| 5,873,835 A | 2/1999 | Hastings et al. | |
| 5,879,283 A | 3/1999 | Adams et al. | |
| 5,935,081 A | 8/1999 | Kadhiresan | |
| 5,956,292 A | 9/1999 | Bernstein | |
| 5,957,950 A | 9/1999 | Mockros et al. | |
| 5,967,986 A | 10/1999 | Cimochowski et al. | |
| 6,044,298 A | 3/2000 | Salo et al. | |
| 6,053,873 A | 4/2000 | Govari et al. | |
| 6,058,329 A | 5/2000 | Salo et al. | |
| 6,068,589 A | 5/2000 | Neukermans | |
| 6,082,367 A | 7/2000 | Greeninger et al. | |
| 6,140,740 A | 10/2000 | Porat et al. | |
| 6,141,588 A | 10/2000 | Cox et al. | |
| 6,185,452 B1 | 2/2001 | Schulman et al. | |
| 6,223,081 B1 | 4/2001 | Kerver | |
| 6,409,675 B1 * | 6/2002 | Turcott | 600/508 |
| 6,475,170 B1 | 11/2002 | Doron et al. | |
| 6,477,406 B1 | 11/2002 | Turcott | |
| 6,480,733 B1 | 11/2002 | Turcott | |
| 6,486,588 B2 | 11/2002 | Doron et al. | |
| 6,504,286 B1 | 1/2003 | Porat et al. | |
| 6,527,729 B1 | 3/2003 | Turcott | |
| 6,537,200 B2 | 3/2003 | Leysieffer et al. | |
| 6,554,761 B1 | 4/2003 | Puria et al. | |
| 6,575,894 B2 | 6/2003 | Leysieffer et al. | |
| 6,600,949 B1 | 7/2003 | Turcott | |
| 6,628,989 B1 | 9/2003 | Penner et al. | |
| 6,629,922 B1 | 10/2003 | Puria et al. | |
| 6,629,951 B2 * | 10/2003 | Laufer et al. | 604/96.01 |
| 6,643,548 B1 | 11/2003 | Mai et al. | |
| 6,645,145 B1 | 11/2003 | Dreschel et al. | |
| 6,654,638 B1 | 11/2003 | Sweeney | |
| 6,671,550 B2 | 12/2003 | Iaizzo et al. | |
| 6,697,674 B2 | 2/2004 | Leysieffer | |
| 6,720,709 B2 | 4/2004 | Porat et al. | |
| 6,740,076 B2 | 5/2004 | Hoben et al. | |
| 6,741,714 B2 | 5/2004 | Jensen | |
| 6,763,722 B2 | 7/2004 | Fjield et al. | |
| 6,764,446 B2 | 7/2004 | Wolinsky et al. | |
| 7,016,739 B2 | 3/2006 | Bange et al. | |
| 7,024,248 B2 | 4/2006 | Penner et al. | |
| 7,035,684 B2 | 4/2006 | Lee | |
| 7,107,103 B2 | 9/2006 | Schulman et al. | |
| 7,220,232 B2 | 5/2007 | Suorsa et al. | |
| 7,228,175 B2 | 6/2007 | Jain et al. | |
| 7,236,821 B2 | 6/2007 | Cates | |
| 7,283,874 B2 | 10/2007 | Penner | |
| 7,335,169 B2 | 2/2008 | Thompson et al. | |
| 7,522,962 B1 | 4/2009 | Doron et al. | |
| 7,615,012 B2 * | 11/2009 | Von Arx et al. | 600/528 |
| 7,634,318 B2 | 12/2009 | Tran et al. | |
| 2002/0027400 A1 | 3/2002 | Toda | |
| 2002/0036446 A1 | 3/2002 | Toda et al. | |
| 2002/0151938 A1 | 10/2002 | Corbucci | |
| 2002/0177782 A1 | 11/2002 | Penner | |
| 2003/0055461 A1 | 3/2003 | Girouard et al. | |
| 2004/0103906 A1 | 6/2004 | Schulman et al. | |
| 2004/0106954 A1 | 6/2004 | Whitehurst et al. | |
| 2004/0106960 A1 | 6/2004 | Siejko et al. | |
| 2004/0106961 A1 | 6/2004 | Siejko et al. | |
| 2004/0122315 A1 | 6/2004 | Krill | |
| 2004/0122484 A1 | 6/2004 | Hatlestad et al. | |
| 2004/0127792 A1 | 7/2004 | Siejko et al. | |
| 2004/0138572 A1 | 7/2004 | Thiagarajan | |
| 2004/0167416 A1 | 8/2004 | Lee | |
| 2004/0204744 A1 | 10/2004 | Penner et al. | |
| 2004/0230249 A1 | 11/2004 | Haefner | |
| 2004/0260214 A1 | 12/2004 | Echt et al. | |
| 2005/0102001 A1 | 5/2005 | Maile et al. | |
| 2005/0131472 A1 | 6/2005 | Ding et al. | |
| 2005/0137490 A1 | 6/2005 | Scheiner et al. | |
| 2005/0148896 A1 | 7/2005 | Siejko et al. | |
| 2005/0149136 A1 | 7/2005 | Siejko et al. | |
| 2005/0149138 A1 | 7/2005 | Min et al. | |
| 2006/0009818 A1 * | 1/2006 | Von Arx et al. | 607/60 |
| 2006/0082259 A1 | 4/2006 | Schlenke | |
| 2006/0136004 A1 | 6/2006 | Cowan | |
| 2006/0142819 A1 | 6/2006 | Penner et al. | |
| 2006/0149329 A1 * | 7/2006 | Penner | 607/32 |
| 2007/0049977 A1 | 3/2007 | Von Arx et al. | |
| 2007/0055184 A1 | 3/2007 | Echt | |
| 2007/0093875 A1 | 4/2007 | Chavan et al. | |
| 2007/0142728 A1 | 6/2007 | Penner | |

| | | | |
|---|---|---|---|
| 2008/0021289 | A1 | 1/2008 | Zhang et al. |
| 2008/0021509 | A1 | 1/2008 | Mi et al. |
| 2008/0021510 | A1 | 1/2008 | Mi et al. |
| 2010/0004718 | A1 | 1/2010 | Doron et al. |
| 2010/0049269 | A1 | 2/2010 | Tran |
| 2010/0094105 | A1 | 4/2010 | Porat et al. |

FOREIGN PATENT DOCUMENTS

| | | |
|---|---|---|
| EP | 0798016 | 10/1997 |
| EP | 0897690 | 2/1999 |
| EP | 1151719 | 11/2001 |
| WO | WO 83/03345 | 10/1983 |
| WO | WO 97/01986 | 1/1997 |
| WO | WO 97/33513 | 9/1997 |
| WO | 97/35636 | 10/1997 |
| WO | WO 97/47236 | 12/1997 |
| WO | WO 98/26716 | 6/1998 |
| WO | WO 98/29030 | 7/1998 |
| WO | WO 99/26530 | 6/1999 |
| WO | WO 99/59460 | 11/1999 |
| WO | WO 00/16686 | 3/2000 |
| WO | WO 03/068047 | 8/2003 |
| WO | 2004/091719 | 10/2004 |
| WO | WO 2006/069215 | 6/2006 |

OTHER PUBLICATIONS

Robert D. Blevins Ph.D., "Formulas for Natural Frequency and Mode Shape", ISBN: 1-57524-184-6.
Search Report and Written Opinion of PCT/US2007/073989, filed Jul. 20, 2007, both mailed Dec. 20, 2007.
Search Report and Written Opinion of PCT/US2007/073998, filed Jul. 20, 2007, both mailed Mar. 6, 2008.
Blevins Ph.D., "Formulas for Natural Frequency and Mode Shape", ISBN: 1-57524-184-6.
C. Hierold et al (Germany, 1998) "Implantable Low Power Integrated Pressure Sensor System for Minimal Invasive Telemetric Patient Monitoring" IEEE, pp. 568-573.
Cassereau et al., "Time Reversal of Ultrasonic Fields—Part 3: Theory of the Closed Time-Reversal Cavity," IEEE Transactions on Ultrasonics, Ferroelectrics, and Frequency Control, vol. 39, No. 5, Sep. 1992, pp. 579-592.
ER. Cosman et al (Massachussetts, Apr. 1979) "A Telemetric Pressure Sensor for Ventricular Shunt Systems" Surgical Neurology, vol. 11, No. 4, pp. 287-294.
Fink et al., "Time Reversal Acoustics," 2004 IEEE Transactions on Ultrasonics, Ferroelectrics, and Frequency Control Joint 50th Anniversary Conference, Ultrasonics Symposium, pp. 850-859.
Fink, "Time Reversal of Ultrasonic Fields—Part 1: Basic Principles," IEEE Transactions on Ultrasonics, Ferroelectrics, and Frequency Control, vol. 39, No. 5, Sep. 1992, pp. 555-566.
G. W. H. Schurink et al (1998) "Late Endoleak after Endovascular Therapy for Abdominal Aortic Aneurysm" Eur. J. Vasc. Endovasc. Surg. vol. 17, pp. 448-450.
GH White et al (1997) "Endoleak Following Endoluminal Repair of AAA: Management Options and Patient Outcomes", J. Endovasc Surg. p. 1-45.
Karl E. Richard et al (Germany, Jan. 1999) "First clinical results with a telemetric shunt-integrated ICP-sensor" Neurological Research vol. 21, pp. 117-120.
Prof. Dr. Johannes Zacheja et al (Germany, Sep. 1996) "An Implantable Microsystem for Biomedical Applications" Micro System Technologies 96, pp. 717-722.
S. K. Gupta et al (1999) "Use of a Piezoelectric Film Sensor for Monitoring Vascular Grafts" The American Journal of Surgery vol. 160, pp. 182-186.
T. Chuter et al (Sweden, Jan. 1997) "Aneurysm Pressure following Endovascular Exclusion" Eur. J. Vasc. Endovasc. Surg. vol. 13, pp. 85-87.
T.A. Cochran et al (1990) "Aortic Aneurysm Abdominal", Current Therapy in Adult Medicine, Fourth Edition.
Wu et al., "Time Reversal of Ultrasonic Fields—Part 2: Experimental Results," IEEE Transactions on Ultrasonics, Ferroelectrics, and Frequency Control, vol. 39, No. 5, Sep. 1992, pp. 567-578.
Z. Tang et al (May 1995) "Data Transmission from an Implantable Biotelemeter by Load-Shift Keying Using Circuit Configuration Modulator" IEEE Transactions on Biomedical Engineering, vol. 42, No. 5, pp. 524-528.

* cited by examiner

RESONANT STRUCTURES FOR IMPLANTABLE DEVICES

CROSS-REFERENCE TO RELATED APPLICATION

This application claims priority to Provisional Application No. 60/820,057, filed Jul. 21, 2006, which is herein incorporated by reference in its entirety.

TECHNICAL FIELD

The present invention relates to transducers used in combination with an implantable medical device for wireless communication between the implantable medical device and remote devices implanted in the body. The present invention more particularly relates to acoustic transducers used in combination with a metallic cavity implantable medical device.

BACKGROUND

Implantable medical devices are often used to treat a variety of medical conditions. Examples of implantable medical devices include drug delivery devices, pain management devices, and devices that treat heart arrhythmias. One example of an implantable medical device used to treat heart arrhythmias is a cardiac pacemaker, which is commonly implanted in a patient to treat bradycardia (i.e., abnormally slow heart rate). A pacemaker includes a pulse generator and leads, which form the electrical connection between the pulse generator and the heart. An implantable cardioverter defibrillator (ICD) is used to treat tachycardia (i.e., abnormally rapid heart rate). An ICD also includes a pulse generator and leads that deliver electrical energy to the heart. Pulse generators typically include a metallic housing for a battery and electrical circuitry and a header for connecting the leads to the pulse generator.

Implantable medical devices are also useful in the treatment of heart failure. For example, cardiac resynchronization therapy (CRT) (also commonly referred to as biventricular pacing) is an emerging treatment for heart failure, which involves stimulation of both the right and left ventricles to increase hemodynamic efficiency and cardiac output. The treatment of heart failure and heart arrhythmias can be enhanced through the use of remote implanted devices. One example of such a remote device is a pressure sensor located in the vasculature. Communication between the implantable medical device and the remote device can allow the sensor data to be downloaded by a clinician used to modify the therapy delivered by the implantable medical device, or both. There is therefore a need for an implantable medical device that includes a transducer for communication with a remote implanted device.

SUMMARY

The present invention, according to one embodiment, is an implantable medical device comprising a housing and a limiting structure defining a resonant region in the housing. An acoustic transducer is connected to the limiting structure and extends into the resonant region so that the resonant region mechanically amplifies the deformation of the acoustic transducer at a resonant frequency.

The present invention, according to another embodiment, is an implantable medical device comprising a housing and a limiting structure defining a resonant region in the housing. An acoustic transducer having the shape of a beam is mechanically coupled to the limiting structure and partially extends into the resonant region so that the resonant region mechanically amplifies the deformation of the acoustic transducer at a resonant frequency.

The present invention, according to yet another embodiment, is an implantable medical device comprising a housing, an acoustic transducer coupled to the housing, and a means for mechanically amplifying the deformation of the acoustic transducer at a resonant frequency. The means defines a resonant region in the housing.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
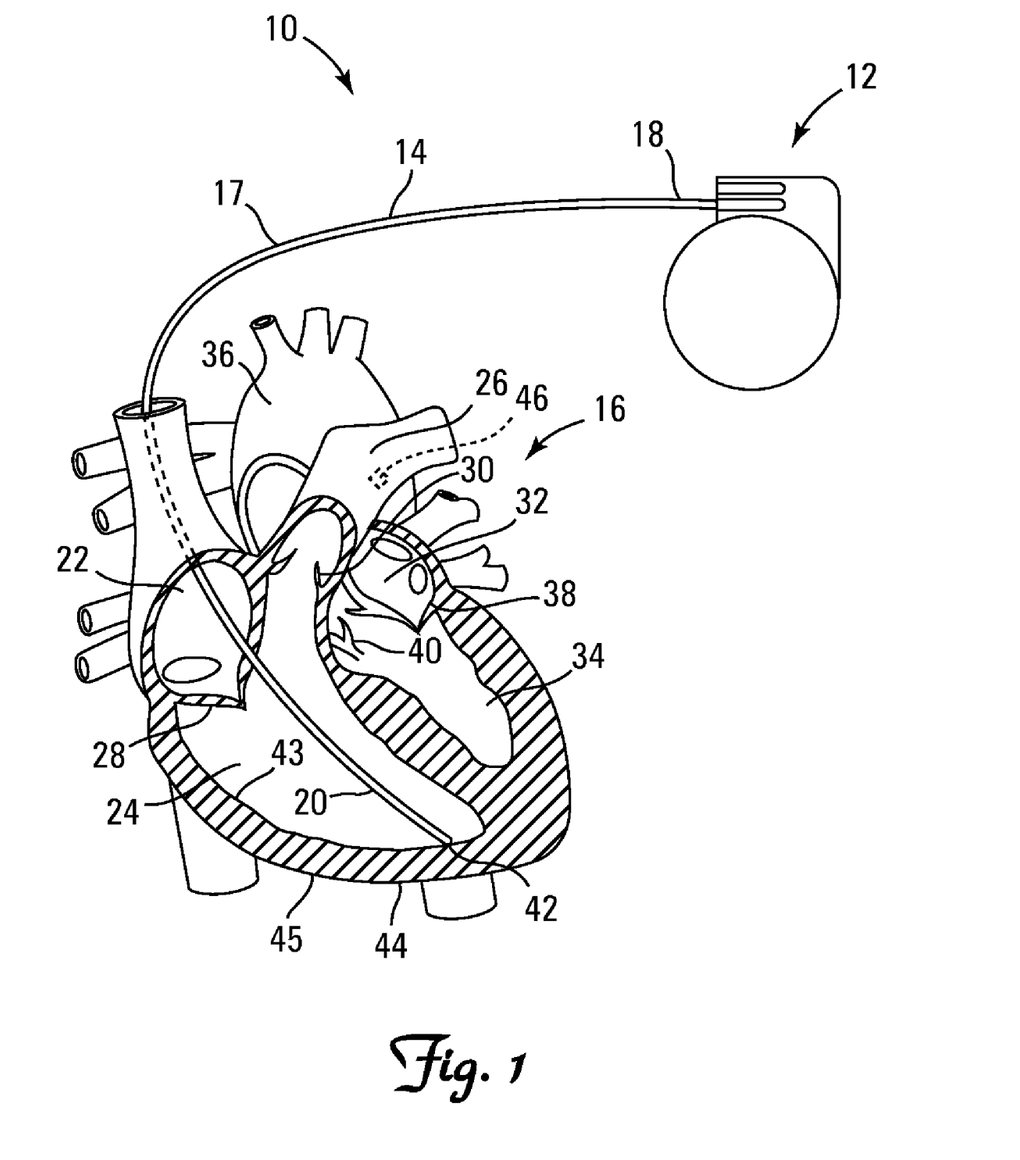
FIG. 1 is a combined cutaway and perspective view of an implantable medical device in accordance with one embodiment of the present invention.

FIG. 1 is a perspective view of an implantable medical device (IMD) 10. The IMD 10 includes a pulse generator 12 and a cardiac lead 14. The lead 14 operates to convey electrical signals between the heart 16 and the pulse generator 12. A proximal end 18 of the lead 14 is coupled to the pulse generator 12 and a distal end 20 is coupled to the heart 16. The lead 14 includes a lead body 17 extending from the lead proximal end 18 to the lead distal end 20.

The heart 16 includes a right atrium 22, a right ventricle 24, and a pulmonary artery 26. A tricuspid valve 28 is located between and controls the flow of blood from the right atrium 22 and the right ventricle 24. A pulmonic valve 30 is located between and controls the flow of blood from the right ventricle 24 to the pulmonary artery 26. The heart 16 also includes a left atrium 32, a left ventricle 34, and an aorta 36. A mitral valve 38 is located between and controls the flow of blood from the left atrium 32 to the left ventricle 34. An aortic valve 40 is located between and controls the flow of blood from the left ventricle 34 to the aorta 36. In one embodiment, the IMD 10 includes a plurality of leads 14. For example, it may include a first lead 14 adapted to convey electrical signals between the pulse generator 12 and the left ventricle 34 and a second lead 14 adapted to convey electrical signals between the pulse generator 12 and the right ventricle 24.

In the embodiment shown in FIG. 1, a helical electrode 42 penetrates the endocardium 43 of the right ventricle 24 and is embedded in the myocardium 44 of the heart 16. When positioned as above, the electrode 42 can be used to sense the electrical activity of the heart 16 or to apply a stimulating pulse to the right ventricle 24. In other embodiments, the cardiac lead 14 of the present invention can also be implanted in any other portion of the heart 16 as known in the art. For example, it may be implanted in the right atrium 22, the right ventricle 24, the pulmonary artery 26, the left ventricle 34, or in the coronary veins. In one embodiment, the IMD 10 includes multiple electrodes 42 disposed to sense electrical activity and/or deliver therapy to both the left and right sides of the heart 16. In one embodiment, the lead 14 can be an epicardial lead where the electrode 42 penetrates the epicardium 45.

As shown in FIG. 1, a remote device 46 is located in the pulmonary artery 26. Alternatively, the remote device 46 could be located in the right ventricle 24, the aorta 36, or any other location in or near the heart 16 or vasculature. The remote device 46 shown in FIG. 1 comprises a pressure sensor. The remote device 46 shown in FIG. 1 can be used to measure pressure in the pulmonary artery 26. In one embodiment, the remote device 46 measures end-diastolic pressure in the pulmonary artery 26. The sensed pressure can be used to predict decompensation of a heart failure patient or to optimize pacing or defibrillation therapy. One example of a pressure sensor 46 adapted to measure pressure is disclosed in U.S. Pat. No. 6,764,446 to Wolinsky et al.

While the IMD 10 shown in FIG. 1 comprises a cardiac pacemaker, in other embodiments, the IMD 10 could comprise any other medical device suitable for implantation in the body. For example, the IMD 10 could comprise a drug delivery device or a pain management device. The remote device 46 can comprise any type of chronically implanted device or remote sensor adapted to deliver therapy or monitor biological functions. The remote device 46 can be located anywhere in the body adapted for sensing a desired biological parameter or delivering therapy. For example, the remote device 46 could comprise a volume sensor or sense any other cardiac parameter, such as maximum or minimum pressure, or calculate a cardiac parameter derivative, such as the slope of the pressure. In other embodiments, the remote device 46 could comprise a glucose level monitor, a pulmonary sound sensor, a satellite pacing device, or any other remote sensing or therapy-delivering device. A plurality of remote devices 46 could be implanted throughout the body and in wireless communication with each other and with an IMD 10.

Figure 2:
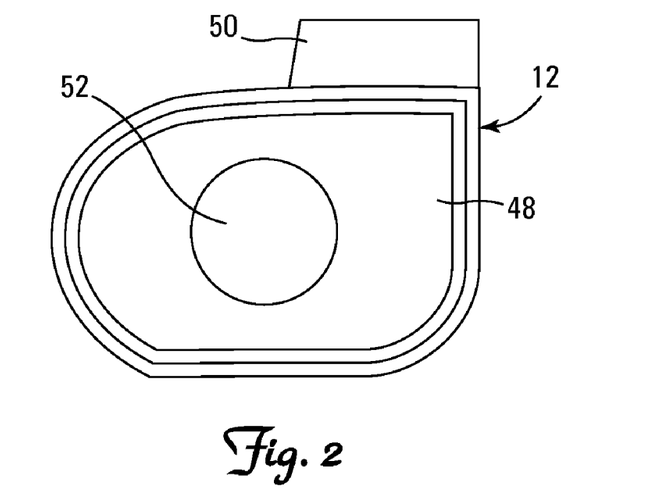
FIG. 2 is a front view of the inside of the implantable medical device of FIG. 1 in accordance with one embodiment of the present invention.
Figure 3A:
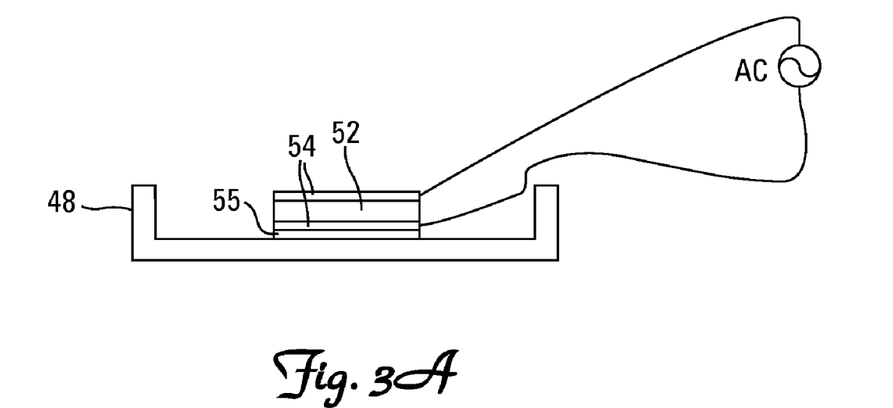
FIGS. 3A-3B depict various views of the implantable medical device of FIG. 2.
Figure 3B:
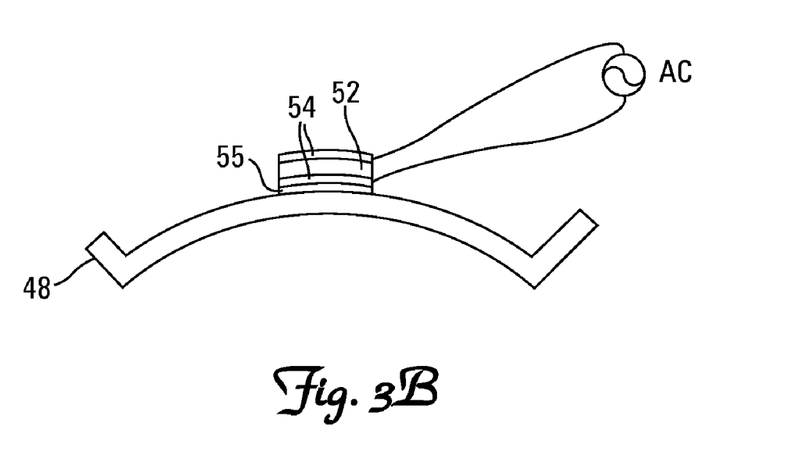

FIG. 2 depicts a front view of the inside of the pulse generator 12. The pulse generator 12 includes a housing 48 and a header 50. An acoustic transducer 52 is attached to the inside of the housing 48 and is electrically connected to control circuitry (not shown). The acoustic transducer 52 can be used as a sensor, an actuator, or as both a sensor and an actuator. FIGS. 3A-3B depict cross-sectional views of the housing 48. The acoustic transducer 52 includes electrodes 54 and can be coupled to the inside of the housing 48 by an insulating bonding layer 55. In the embodiment shown in FIG. 2, the acoustic transducer 52 has a circular shape, but the acoustic transducer could take any other shape, such as rectangular, beam-shaped, circular, annular, or triangular.

In one embodiment, the acoustic transducer 52 comprises a piezoelectric material. Piezoelectric materials adapted for use in the acoustic transducer 52 include piezo polymer, piezo crystal, or piezo ceramic materials. In one embodiment, the acoustic transducer 52 can comprise a polyvinylidine difluoride (PVDF) material. In another embodiment, the acoustic transducer 52 can comprise a lead zirconate titanate (PZT) material. In yet another embodiment, the acoustic transducer can comprise a piezo single crystal material, such as lead magnesium niobate-lead titanate (PMN-PT). In other embodiments, the acoustic transducer 52 can comprise a cMUT transducer. In one embodiment where a PZT material is used, the thickness of the PZT material is approximately equivalent to the thickness of the housing 48. In one embodiment, the acoustic transducer 52 comprises PZT5A material, has a diameter of 25.4 millimeters or less, and has a thickness of 3 millimeters or less.

As shown in FIGS. 3A-3B, one electrode 54 is connected to an AC voltage source and the other electrode 54 is connected to ground. (The thickness of the electrodes 54 in the Figures is not shown to scale.) The AC voltage can be applied to the acoustic transducer 52 to cause it to vibrate at a desired frequency. Alternatively, both electrodes 54 could be driven simultaneously by an H-bridge, as is known to one of skill in the art. In one embodiment, the acoustic transducer 52 has a mechanical resonance of greater than approximately 20 kiloHertz. In another embodiment, the acoustic transducer 52 has a mechanical resonance at a frequency of approximately 40 kiloHertz. In yet another embodiment, the acoustic transducer 52 can operate in an electrically resonant mode.

In one embodiment, the acoustic transducer 52 is adapted to generate and receive acoustic waves having a frequency greater than approximately 20 kiloHertz, has a transmit sensitivity greater than approximately 100 Pascals per Volt at 0.25 meters of water or transmitting voltage response (TVR) greater than approximately 148 decibels (dB) referenced to (re) 1 microPascal per Volt at 1 meter of water, has a receive sensitivity greater than approximately 0.5 milliVolt per Pascal or free-field voltage sensitivity (FFVS) greater than −186 dB re 1 Volt per microPascal, and has a total static capacitance less than or equal to approximately 20 nanoFarads. In another embodiment, the acoustic transducer 52 is adapted to generate and receive acoustic waves having a frequency of approximately 40 kiloHertz, has a transmit sensitivity greater than approximately 200 Pascals per Volt at 0.25 meters of water or TVR greater than approximately 154 decibels re 1 microPascal per Volt at 1 meter of water, has a receive sensitivity greater than approximately 0.5 milliVolts per Pascal or FFVS greater than −186 dB re re 1 Volt per microPascal, and a total static capacitance less than or equal to approximately 8 nanoFarads.

The acoustic transducer 52 can be used for wireless communication between the IMD 10 and the remote device 46. As shown in FIG. 3B, acoustic signals are transmitted from the IMD 10 to the remote device 46 by applying an AC voltage or a charge change to the acoustic transducer 52 so that the acoustic transducer 52 deforms and the pulse generator housing 48 vibrates in response to the deformation. Acoustic signals sent from the remote device 46 are received by the acoustic transducer 52 when an impinging acoustic wave results in mechanical vibration of the housing 48, thus causing a voltage change or a charge density change in the acoustic transducer 52, which is detected by control circuitry (not shown).

Figure 4A:
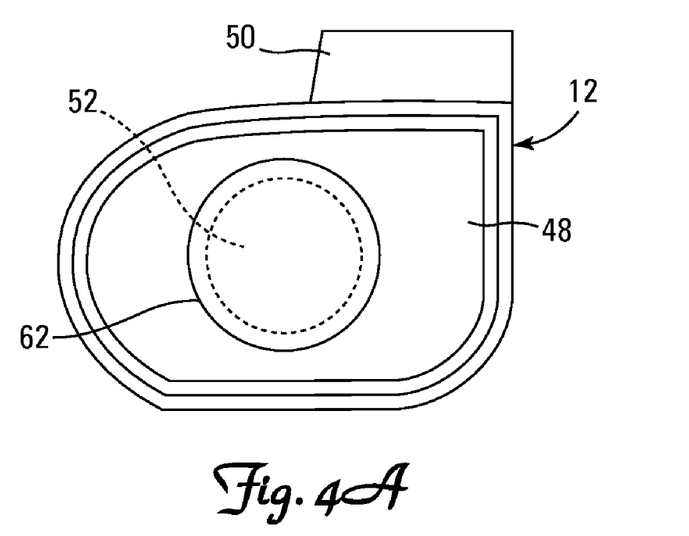
FIGS. 4A-4B are various views of an implantable medical device in accordance with another embodiment of the present invention.
Figure 4B:
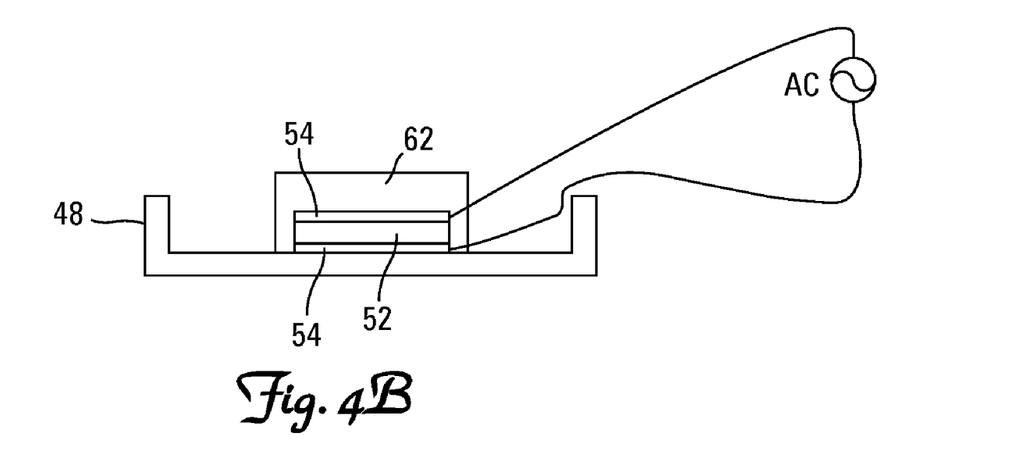

FIGS. 4A-4B depict an embodiment of the present invention where a casing 62 encloses the acoustic transducer 52. The casing 62 serves two functions. First, it bends when the acoustic transducer 52 deforms, thereby applying a bending moment to the housing 48. Second, it mechanically amplifies the deformation of the acoustic transducer 52, particularly when the housing 48 has a resonant mode at the desired frequency. In one embodiment, the casing 62 has a diameter of greater than 25 millimeters, a height of less than 4 millimeters, a top thickness of between 0.2 and 1 millimeter, and a wall thickness of between 3 to 6 millimeters. In one embodiment, the acoustic transducer 52 is attached to the casing 62 and there may be a gap or space between the acoustic transducer 52 and the housing 48. In another embodiment, the acoustic transducer 52 is attached to the housing 48 and there may be a gap between the acoustic transducer 52 and the casing 62.

Figures 5A, 5B:
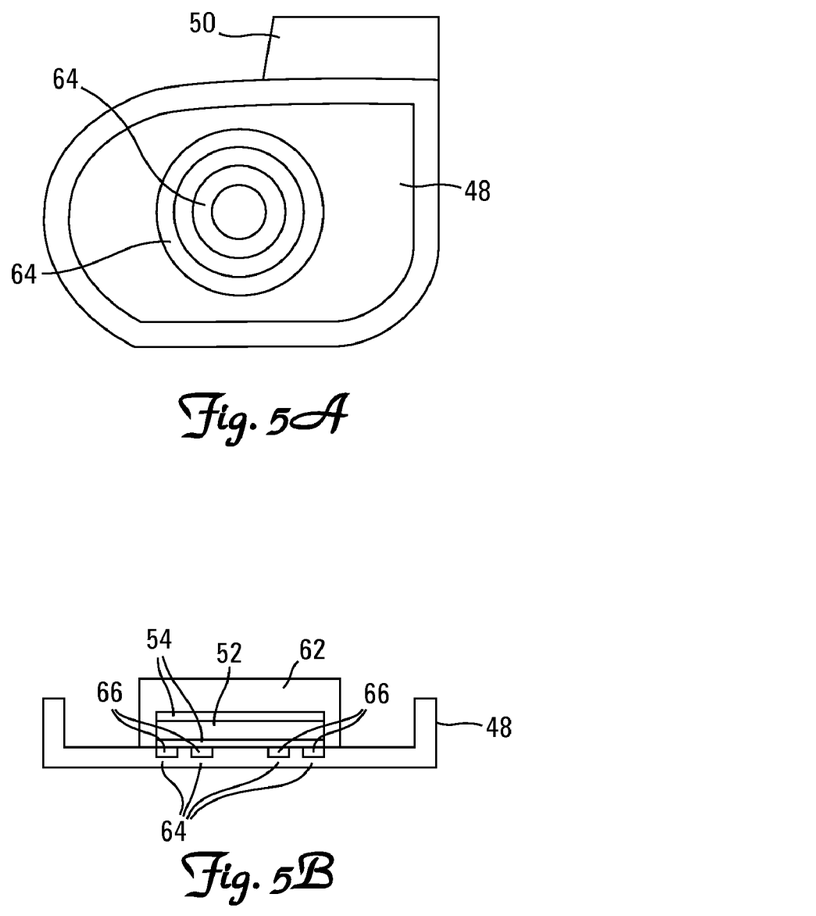
FIGS. 5A-5B are various views of an implantable medical device in accordance with yet another embodiment of the present invention.
Figure 6:
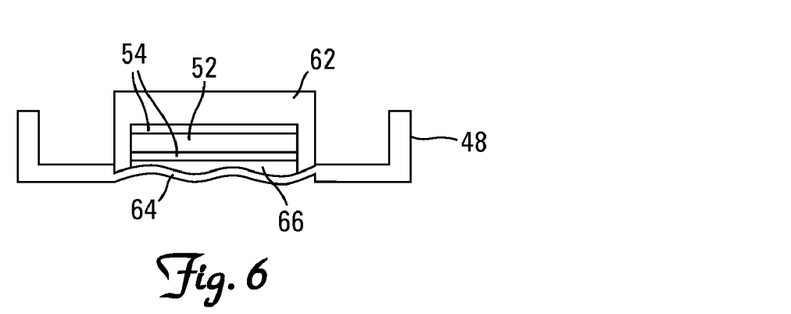
FIG. 6 is a cross-sectional view of an implantable medical device in accordance with another embodiment of the present invention.

FIGS. 5A-5B and 6 depict alternative embodiments of an IMD 10 having an acoustic transducer 52. As shown in FIGS. 5A-5B, the housing 48 includes annular regions 64 having a thinner cross-section than a substantial portion of the housing 48. The regions 64 shown in FIG. 5A comprise a "bull's eye" but alternatively could have any other shape, including a plurality of rectangles or circles. As shown in FIG. 5B, the acoustic transducer 52 is adjacent to the regions 64, thereby allowing for increased vibration, movement, and/or deformation of the housing 48. In one embodiment, the thickness of the regions 64 is approximately 0.12 millimeter. FIG. 6 depicts an alternative housing 48 where the region 64 takes the form of a corrugated or wavy region of the housing 48 located underneath the acoustic transducer 52. The gaps 66 shown in FIGS. 5A-5B and 6 can contain air, nitrogen, some other gas, or vacuum. As shown, FIGS. 5A-5B and 6 include the casing 62 described with respect to FIGS. 4A-4B, but in alternative embodiments, the casing 62 need not be present.

Figure 7A:
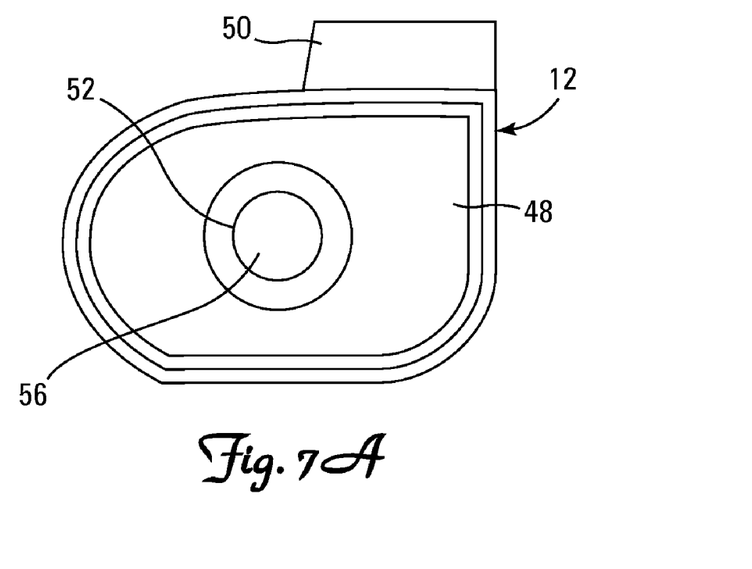
FIGS. 7A-7B are various views of an implantable medical device in accordance with another embodiment of the present invention.
Figure 7B:
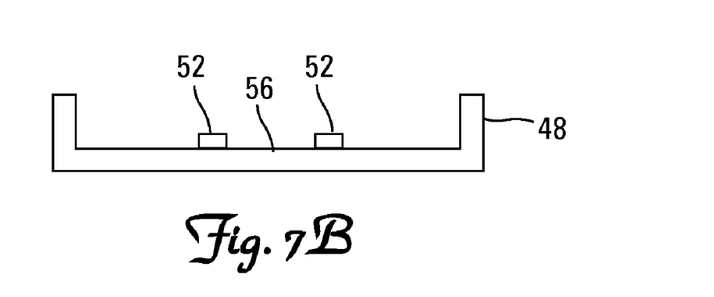

FIGS. 7A-7B depict an alternative embodiment of an IMD 10 having an acoustic transducer 52. In this embodiment, the acoustic transducer 52 has an annular shape. The acoustic transducer 52 acts as a limiting structure and defines the resonance characteristics of the region 56 by establishing boundary conditions for the region 56. The resonance characteristics of the region 56 enhance the performance of the acoustic transducer 52. When acoustic waves having the same frequency as the resonant frequency of the region 56 impact the region 56, the region 56 vibrates, resulting in deformation of the acoustic transducer 52. This deformation results in a voltage or a charge change in the acoustic transducer 52, which is detected by the control circuitry. Driving the acoustic transducer 52 using an AC voltage or an H-bridge at the resonant frequency results in periodic deformation of the acoustic transducer 52. This deformation causes the region 56 to vibrate at the resonant frequency, thereby transmitting an acoustic wave from the region 56 at the desired frequency.

The dimensions of the acoustic transducer 52 can be determined using the following formula from Blevins, "Formulas for Natural Frequencies and Mode Shapes", ISBN 1-57524-184-6, herein incorporated by reference in its entirety:

$$f = \frac{\lambda^2}{2 \cdot \pi \cdot a^2} \sqrt{\frac{E \cdot h^3}{12 \cdot \gamma \cdot (1 - v^2)}}$$

As used in the above equation, a is the plate radius, h is the plate thickness, E is Young's modulus, ν is Poisson's ratio, ρ is the density, γ is the mass per unit area or ρ*h, and λ is a dimensionless frequency parameter dependent on the mode shape that can be found in Blevins.

In one embodiment, the acoustic transducer 52 comprises a PZT material and defines a region 56 having a mechanical resonance of greater than approximately 20 kiloHertz. In one embodiment where the housing 48 comprises titanium and λ=3.19 for mode 00, E=116 GigaPascals, ν=0.3, h=0.3 millimeters, and ρ=4500 kg/m$^3$, and a=4.2 millimeters, for an annular piezoelectric transducer 52 with an inner radius of 4.2 millimeters, an outer radius of 8.4 millimeters, and a thickness of 2 millimeters, the natural frequency f of the first mode of the region 56 is at 40 kHz. The acoustic transducer 52 can be bonded to the housing 48 using epoxy or medical adhesive. Blevins provides additional mode resonant frequency formulas for additional shapes and boundary conditions.

Figure 8:
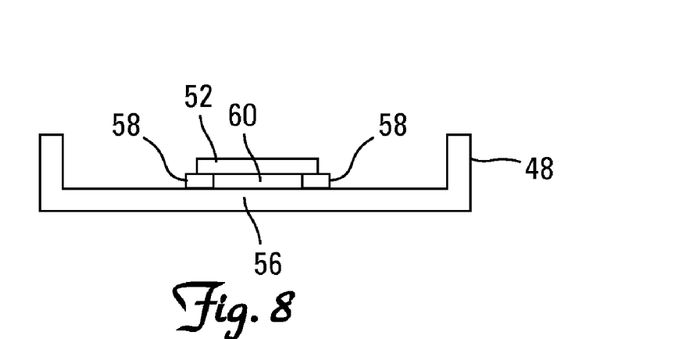
FIG. 8 is a cross-sectional view of an implantable medical device in accordance with yet another embodiment of the present invention.

In the embodiment shown in FIG. 8, the acoustic transducer 52 is mechanically bonded to a non-active limiting structure 58. As shown, the limiting structure 58 has an annular shape and defines the resonant region 56. Use of the non-active limiting structure 58 improves both the transmit and receive sensitivity of the acoustic transducer 52 when the resonant region 56 which has the same resonant frequency as the acoustic transducer 52. The non-active limiting structure 58 transfers deformation between the acoustic transducer 52 and the housing 48. For example, when the acoustic transducer 52 is in a receive mode, an impinging acoustic wave causes the resonant region 56 to vibrate, and the resulting deformation is transferred to the acoustic transducer 52 through the non-active limiting structure 58. When the acoustic transducer 52 is in a transmit mode, actuation of the acoustic transducer 52 causes it to vibrate at the resonant frequency, which is then transferred to the housing 48 by the non-active limiting structure 58, thus causing the resonant region 56 to vibrate at the resonant frequency. The non-active limiting structure 58 can be comprised of titanium, aluminum, stainless steel, ceramic material, or any other rigid material. The gap 60 between the acoustic transducer 52 and the resonant region 56 can be filled with air, nitrogen, some other gas, or vacuum.

Figure 9A:
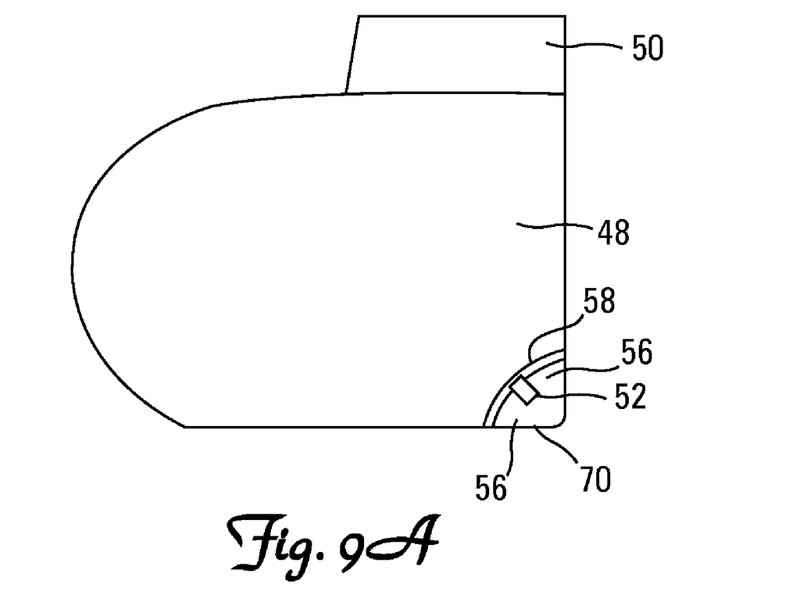
FIGS. 9A-9B are various views of an implantable medical device in accordance with another embodiment of the present invention.
Figure 9B:
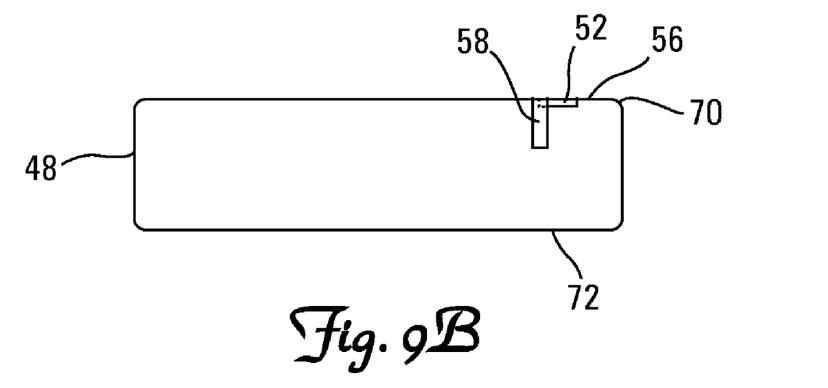

FIGS. 9A-9B depict an alternative embodiment of the IMD 10. As shown in FIG. 9A, the limiting structure 58 is located in a corner 70 of the housing 48, has an approximately semicircular shape, and defines a resonant region 56. The acoustic transducer 52 is bonded to the housing 48 and extends from the limiting structure 58 into the resonant region 56. In one embodiment, the length of the acoustic transducer 52 is determined by the strain/stress profile of the resonant region 56. In one embodiment, the deformation of the acoustic transducer 52 is constrained by the limiting structure 58 and the acoustic transducer 52 has a length of no more than half of the radius of the resonant region 56. As shown in the cross-sectional view of FIG. 9B, the limiting structure 58 does not extend to the rear wall 72 of the housing, but in an alternative embodiment, the limiting structure 58 could extend to the rear wall 72. In yet another alternative embodiment, the limiting structure 58 could be located on the outside of the housing 48. In one embodiment, the limiting structure 58 could take the shape of an annular ring located on the outside of the housing 48.

Figure 10A:
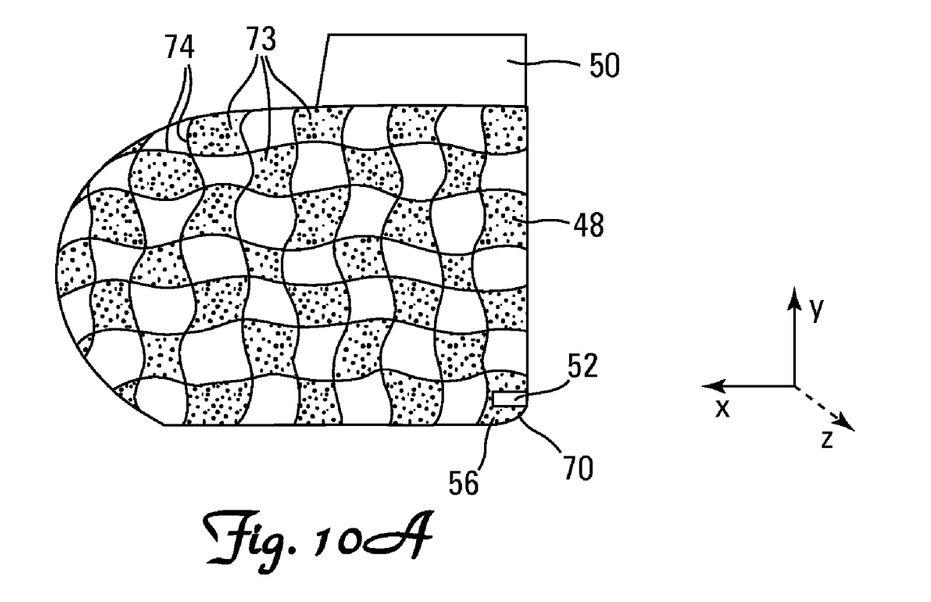
FIGS. 10A-10B are various views of an implantable medical device in accordance with another embodiment of the present invention.
Figure 10B:
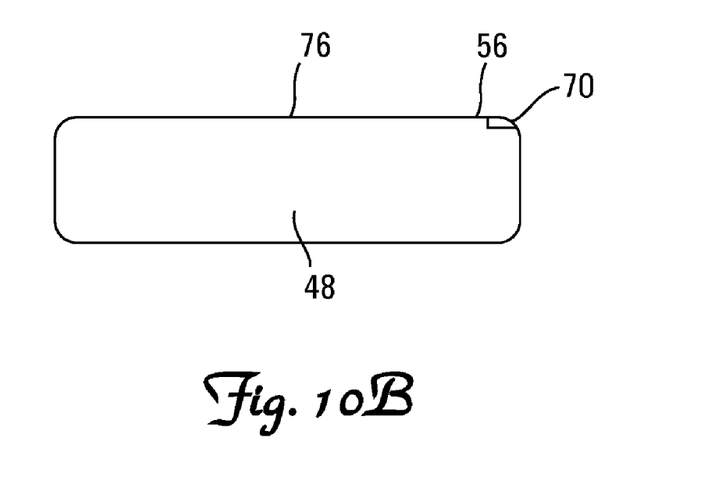

FIGS. 10A-10B depict yet another alternative embodiment of the present invention. In this embodiment, the acoustic transducer 52 is located in the corner 70 of the housing 48. The checkerboard pattern shown in FIG. 10A represents the mode shape of the housing 48 at approximately 40 kiloHertz. The regions 73 represent regions of the housing 48 that are moving in the Z-axis. These regions 73 can be moving either in a positive or negative direction along the Z-axis. The dotted regions 73 can be moving in a positive direction along the Z-axis while the undotted regions can be moving in a negative direction along the Z-axis. The lines 74 of the checkerboard pattern represent the nodal regions, or lines where the housing is motionless with respect to the Z-axis. In the embodiment shown, the corner 70 acts as a limiting structure and defines a resonant region 56, but in other embodiments, the transducer 52 could be located in a region 73 where the nodal lines 74 create a resonant region 56. As shown, the acoustic transducer 52 is bonded to the top face 76 and is located in the resonant region 56. In one embodiment, the acoustic transducer 52 is located in a region of maximum stress and strain. In other embodiments, the shape of the housing 48 itself can be changed to obtain a desired frequency characteristic. In other embodiments, the housing 48 could be embossed or include a "dimple" to obtain a desired frequency characteristic.

Figure 11A:
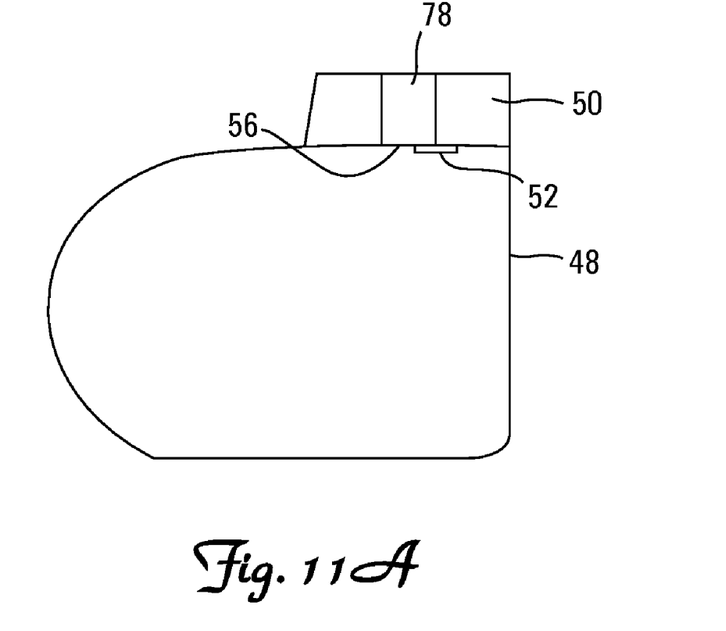
FIGS. 11A-11B are various views of an implantable medical device in accordance with another embodiment of the present invention.
Figure 11B:
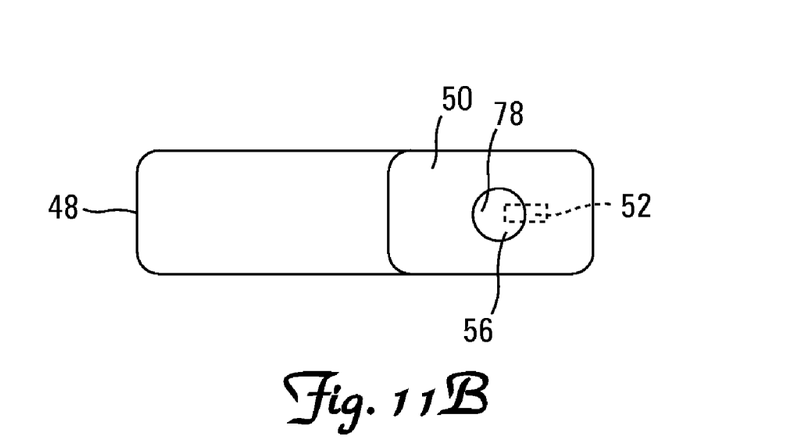

FIGS. 11A-11B show another alternative embodiment of the IMD 10 of the present invention. In this embodiment, the header 50 acts as a limiting structure on the acoustic transducer 52. An aperture 78 is located in the header 50 and defines a resonant region 56. The acoustic transducer 52 extends into the resonant region 56 and is bonded to the inside of the housing 48.

Figure 12:
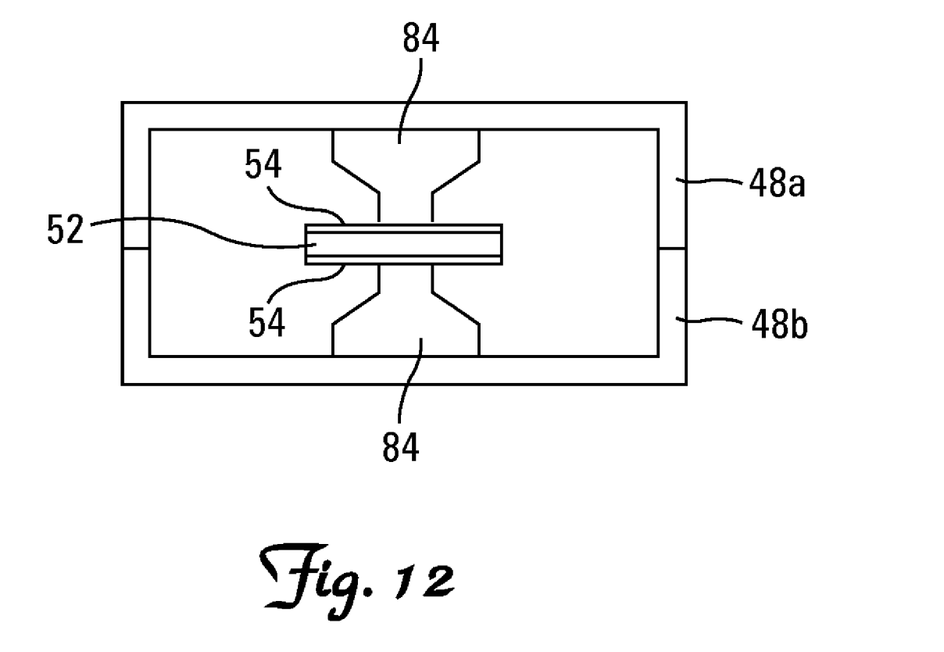
FIG. 12 is a cross-sectional view of an implantable medical device in accordance with yet another embodiment of the present invention.

FIG. 12 shows a cross-sectional view of an alternative embodiment of the IMD 10 of the present invention. The IMD 10 includes a housing 48 having an upper portion 48a and lower portion 48b. A connection rod 84 is coupled to the upper portion 48a and a second connection rod 84 is coupled to the lower portion 48b. An acoustic transducer 52 is interposed between the two connection rods 84. The connection rods 84 have a bell shape in FIG. 12, but could have any other shape. When the acoustic transducer 52 of FIG. 12 is actuated, the portions 48a, 48b will vibrate, propagating acoustic waves in two directions. The thickness of the acoustic transducer 52 can be adjusted according to the desirable actuation displacement of the housing 48 for generation of acoustic waves.

Figure 13:
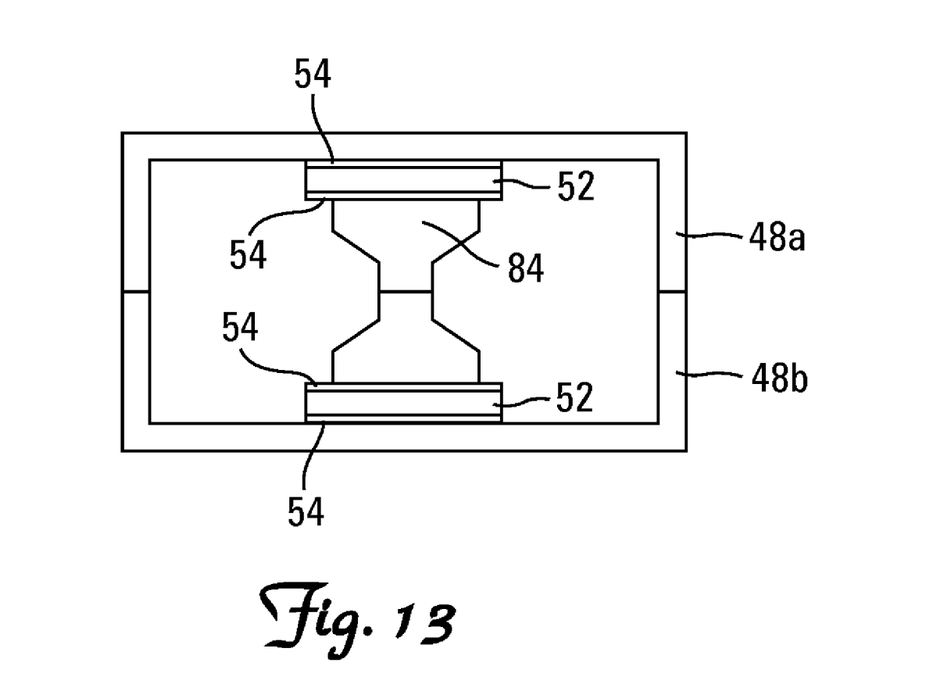
FIG. 13 is a cross-sectional view of an implantable medical device in accordance with yet another embodiment of the present invention.

FIG. 13 shows a cross-sectional view of an alternative embodiment where an acoustic transducer 52 is coupled to each portion 48a, 48b and two connection rods 84 are interposed between the acoustic transducers 52. The structure depicted in FIG. 13 also allows acoustic waves to propagate in two directions simultaneously. The symmetrical design of FIG. 13 allows for easier design and manufacture of the acoustic transducers 52 and connection rods 84.

The embodiments shown in FIGS. 12 and 13 increase the sensitivity of the acoustic transducer or transducers 52. The acoustic transducer or transducers 52 can comprise a piezoelectric material such as PZT or PVDF. In FIGS. 12 and 13, the portions 48a, 48b can apply a pre-stress to the acoustic transducer or transducers 52. In one embodiment, the acoustic transducer or transducers 52 and connection rods 84 are resonant in the thickness mode. In another embodiment, the acoustic transducer or transducers 52 and connection rods 84 are resonant in a radial mode. In one embodiment, the combined thickness of the connection rod 84 and the acoustic transducer 52 is approximately half of the wavelength of the communication frequency. In one embodiment, the combined thickness of the connection rod 84 and the acoustic transducer 52 is between 6 and 7 millimeters. In an alternative embodiment, a single connection rod 84 and a single acoustic transducer 52 are interposed between the portions 48a, 48b. In one embodiment, the single acoustic transducer 52 comprises a PZT material 1 centimeter in diameter and 1 millimeter thick. The connection rod 84 has a height of about 6 millimeters, a minimum diameter of 1 centimeter, a maximum diameter of 2.5 centimeters, and a taper beginning at a height of approximately 3 millimeters. In one embodiment, the thickness of the housing 48 is between 0.3 to 2 millimeters and the width of the housing 48 is between about 2.5 to 5 centimeters.

Figure 14:
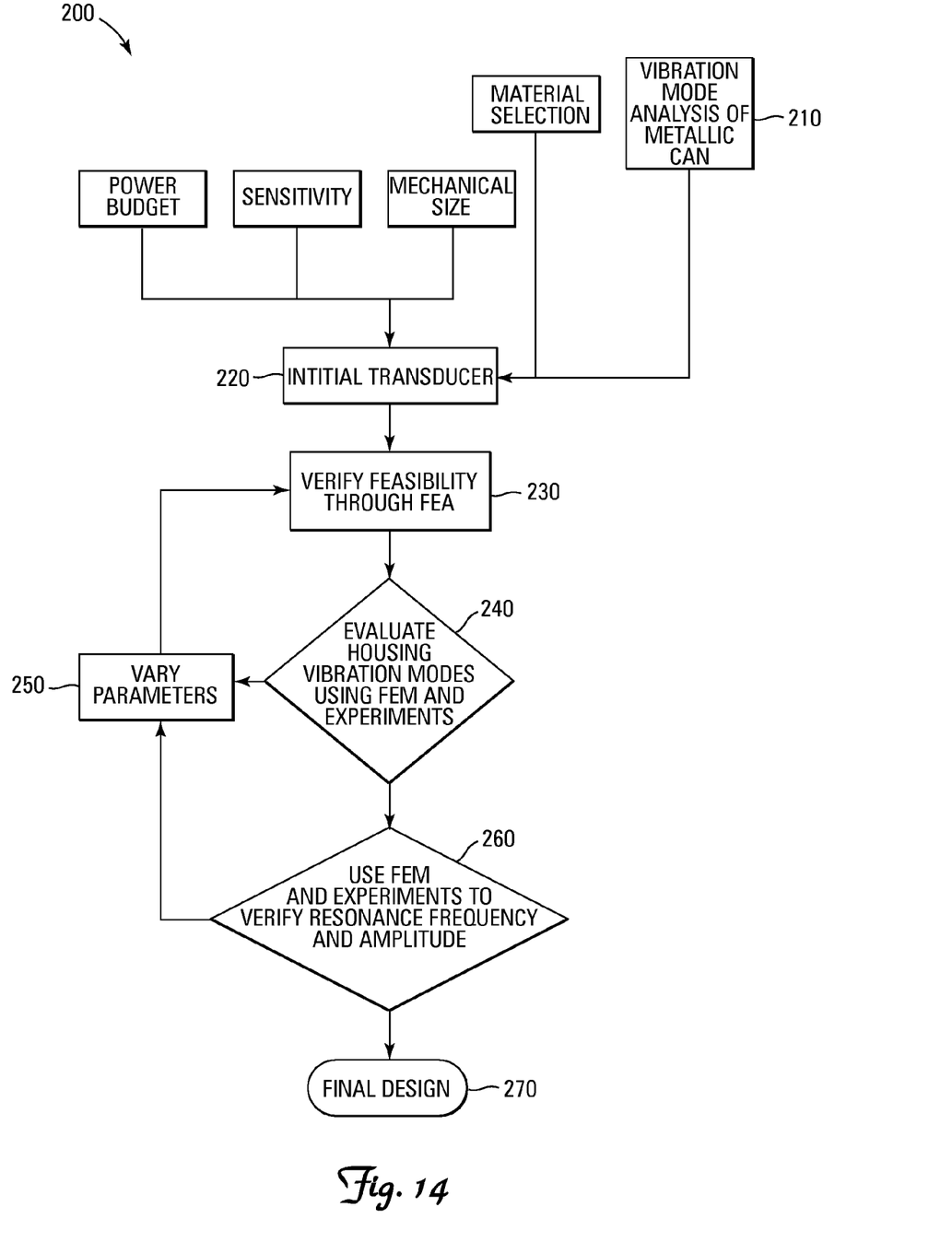
FIG. 14 is a flowchart depicting an exemplary method of optimizing an implantable medical device having an acoustic transducer in accordance with the present invention.

FIG. 14 depicts an exemplary method 200 for optimizing an acoustic transducer 52 and an IMD 10 for wireless communication with a remote device 46. System level requirements such as the power budget, transducer sensitivity, mechanical size, material selection, and the vibration mode of the metallic housing 48 are determined (block 210). An initial acoustic transducer 52 is selected based on the system level requirements (block 220). A Finite Element Methods (FEM) analysis, as is known to those of skill in the art, is performed to verify the feasibility of the initial transducer in simplified geometries (block 230). In this embodiment, verifying the feasibility includes determining whether the acoustic transducer 52 system level attributes fall within an acceptable range for the system level requirements. FEM and water tank experiments are used to determine whether the metallic housing 48 and acoustic transducer 52 have the desired vibration mode at the targeted ultrasonic communication frequency (block 240). The design can be optimized by varying the design of the housing 48, incorporating a casing 62, modifying the design 62 of the casing, modifying the characteristics of the acoustic transducer 52, including the dimensions, or any combination thereof (block 250).

Once the design is further refined, the underwater resonance frequency and amplitude of the acoustic transducer 52 can be verified through Finite Element Method models and water tank experiments (block 260). The experiments can be conducted in a water tank using a hydrophone and can utilize a scanning laser vibrometer (SLV). One such SLV can be obtained from Polytec GmbH, Polytec-Platz 1-7, D-76337 Waldbronn, Germany. The design can again be optimized by varying the parameters such as housing 48 design, acoustic transducer 52 design, etc. (block 250). This optimization is repeated until the desired resonance characteristics are obtained and a final acoustic transducer design is reached (block 270).

The invention has been described with respect to implantable medical devices such as pacemakers and defibrillators, but could be adapted for use in any other implantable medical device, such as an insulin pump, neurostimulator, drug delivery system, pain management system, heart or lung sound sensor, or any other implantable medical device. The remote device 46 can comprise any type of chronically implanted device or remote sensor adapted to deliver therapy or monitor biological functions, such as pressure sensor, glucose level monitor, a pulmonary sound sensor, volume sensor, satellite pacing device, or any other remote sensing or therapy-delivering device, and can be located anywhere in the body adapted for sensing a desired biological parameter or delivering therapy. A plurality of remote devices 46 could be implanted throughout the body and in wireless communication with each other and with an IMD 10.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable medical device comprising:
   a housing having an inside adapted to contain control circuitry of the implantable medical device;
   an annular shaped limiting structure disposed within the inside of the housing and defining a resonant region in the housing; and
   an acoustic transducer connected directly to the limiting structure within the inside of the housing, the acoustic transducer extending into the resonant region so that the resonant region mechanically amplifies the deformation of the acoustic transducer at a resonant frequency.

2. The implantable medical device of claim 1 wherein the limiting structure comprises a non-active structure coupled to an inner side of the housing and the acoustic transducer is located on a top surface of the limiting structure.

3. The implantable medical device of claim 1 wherein the limiting structure comprises a lead zirconate titanate (PZT) material and has an inner diameter of 8.4 millimeters, an outer diameter of approximately 16.8 millimeters, and a thickness of approximately 2 millimeters.

4. The implantable medical device of claim 1 wherein the limiting structure is located in a corner of the housing.

5. The implantable medical device of claim 1 wherein the acoustic transducer has a length of no more than half of a radius of the resonant region.

6. The implantable medical device of claim 1 wherein the limiting structure further comprises a header coupled to the housing.

7. The implantable medical device of claim 1 wherein the resonant region has a resonance greater than approximately 20 kiloHertz.

8. The implantable medical device of claim 1 wherein the resonant region has a resonance of approximately 40 kiloHertz.

9. An implantable medical device comprising:
   a housing and a limiting structure defining a resonant region in the housing; and
   an acoustic transducer having the shape of an elongate beam mechanically coupled directly to the limiting structure and partially extending into the resonant region so that the resonant region mechanically amplifies the deformation of the acoustic transducer at a resonant frequency.

10. The implantable medical device of claim 9 wherein the limiting structure comprises at least a portion of an edge of the housing, the acoustic transducer is connected to the portion, and the resonant region comprises a portion of a mode shape of the housing at the resonant frequency.

11. The implantable medical device of claim 9 wherein the limiting structure comprises a corner of the housing, the acoustic transducer is connected to the corner, and the resonant region comprises a portion of a mode shape of the housing at the resonant frequency.

12. The implantable medical device of claim 9 wherein the acoustic transducer is located in a region of the housing having a maximum stress and maximum strain.

13. The implantable medical device of claim 9 wherein the acoustic transducer comprises a piezoelectric material.

14. The implantable medical device of claim 13 wherein the piezoelectric material comprises polyvinylidine diflouride (PVDF) material.

15. The implantable medical device of claim 13 wherein the piezoelectric material comprises lead zirconate titanate (PZT) material.

16. The implantable medical device of claim 13 wherein the piezoelectric material comprises lead magnesium niobate-lead titanate (PMN-PT).

17. An implantable medical device comprising:
   a housing having an inside adapted to contain control circuitry of the implantable medical device;
   an acoustic transducer coupled to the housing; and
   a means for mechanically amplifying the deformation of the acoustic transducer at a resonant frequency, the means including an annular shaped limiting structure mechanically coupled directly to the acoustic transducer within the inside of the housing and defining a resonant region in the housing.

18. The implantable medical device of claim 17 wherein the means for mechanically amplifying comprises a non-active structure coupled to an inner side of the housing and the acoustic transducer is located on a top surface of the limiting structure.

* * * * *